US00PP27951P3

(12) United States Plant Patent
Randag

(10) Patent No.: US PP27,951 P3
(45) Date of Patent: Apr. 25, 2017

(54) CALLA LILY PLANT NAMED 'FOREVER'

(50) Latin Name: *Zantedeschia sprengeri*
Varietal Denomination: Forever

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 80 days.

(21) Appl. No.: 14/544,438

(22) Filed: Jan. 6, 2015

(65) Prior Publication Data

US 2015/0296689 P1 Oct. 15, 2015

Related U.S. Application Data

(60) Provisional application No. 61/964,771, filed on Apr. 11, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV—International Union for the Protection of New Varieties of Plants: PLUTO Plant Variety Database; May 27, 2016; cultivar name—'Forever' (1 pg).*

* cited by examiner

*Primary Examiner* — Susan McCormick Ewoldt
(74) *Attorney, Agent, or Firm* — The Webb Law Firm

(57) ABSTRACT

'Forever' is a new variety of calla lily having inflorescences with a pink-colored spathe that produces 5-20 inflorescences per tuber. The inflorescence stems are about 30 cm in height. The leaves are green without whitish spots and have a leathery texture.

3 Drawing Sheets

Botanical classification: *Zantedeschia sprengeri*.
Varietal denomination: 'FOREVER'.

BACKGROUND OF THE NEW PLANT

The present invention comprises a new and distinct cultivar of calla lily, botanically known as *Zantedeschia sprengeri* and hereinafter referred to by the cultivar name 'Forever'.

'Forever' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* 'Swan Lake' (female parent, unpatented) with a *Zantedeschia sprengeri* selection referred to as C04011 (male parent, unpatented). 'Forever' was selected in 2007 by the inventor in 't Zand, The Netherlands as one flowering plant within the progeny of the stated cross.

The first act of asexual reproduction of 'Forever' by tissue culture was performed by the inventor in September of 2009 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Forever' which, in combination, distinguish this calla lily as a new and distinct cultivar:

1. Pink-colored spathe;
2. Absence of white spots on leaves; and
3. High inflorescence production.

Further, when compared to calla lily plant named 'Samur' (unpatented), the new variety differs in spathe color. The spathe color of the upper surface of 'Samur' varies between Red-Purple group RHS 68B and 68D, whereas the spathe color of the upper surface of 'Forever' varies between Red-Purple Group RHS 58A and 58B.

Table 1 provides similarities and differences of 'Forever' to its parents, *Zantedeschia sprengeri* 'Swan Lake' and selection C04011.

TABLE 1

| 'Forever' | Similarities | Differences |
|---|---|---|
| 'Swan Lake' | Spathe shape<br>Plant height | Spathe color (White Group RHS 155D)<br>Number of inflorescences (4-10) |
| C04011 | Number of inflorescences<br>Spathe color | Spathe shape (Funnel)<br>Plant height (5-35 cm) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
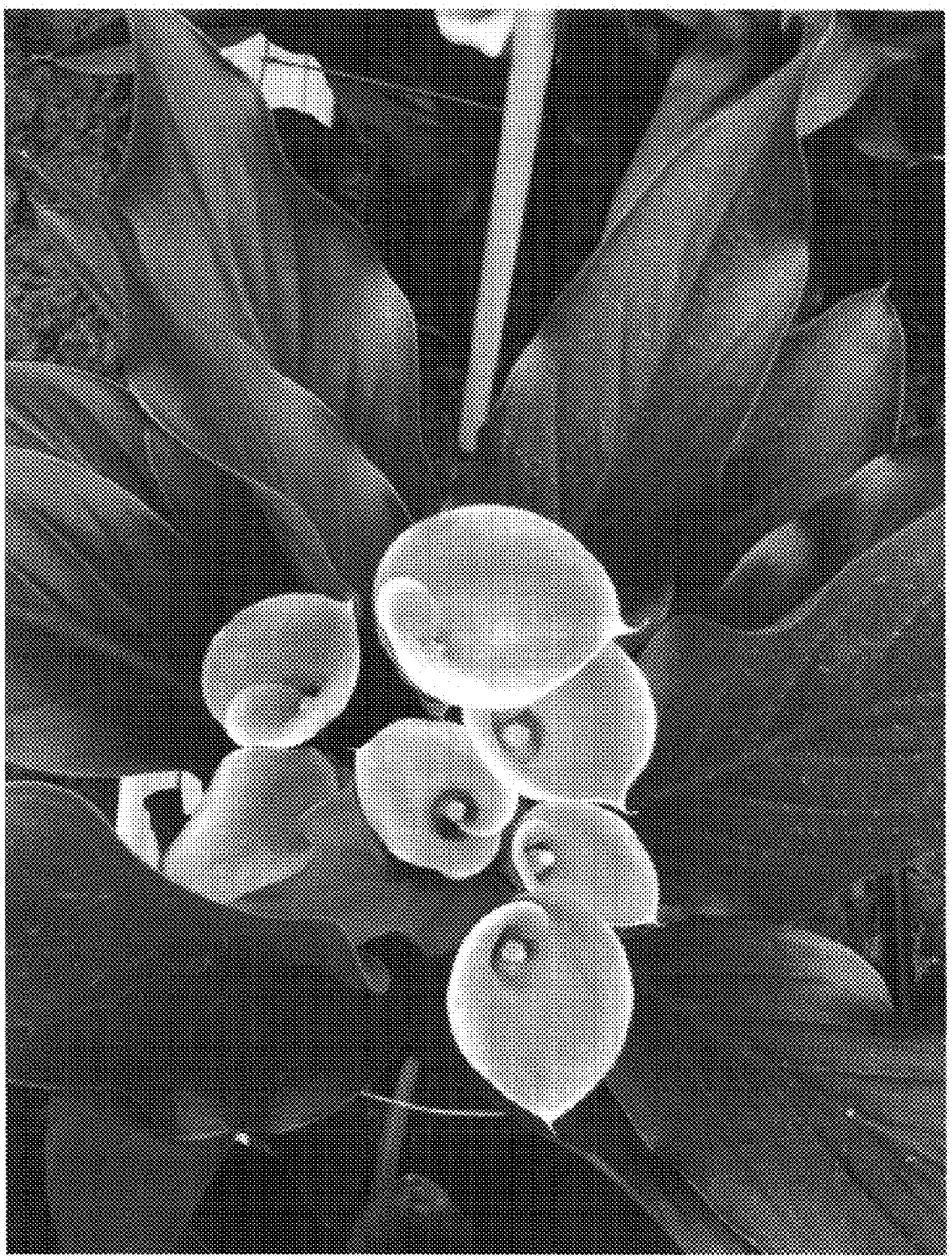
FIG. 1 is an overhead view of a single plant of the new variety.
Figure 2:
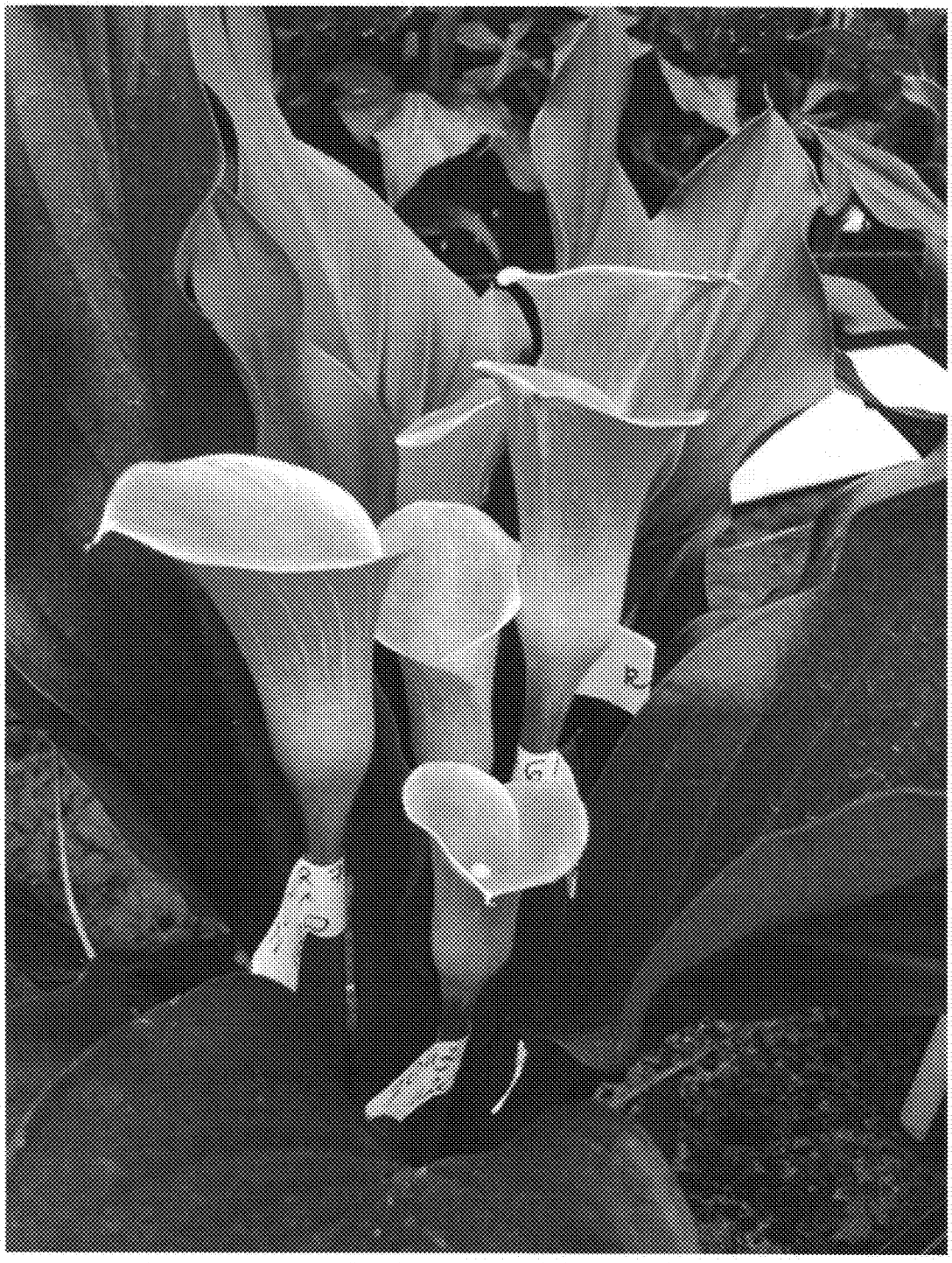
FIG. 2 is a photograph of a side view of a single plant of the new variety.
Figure 3:
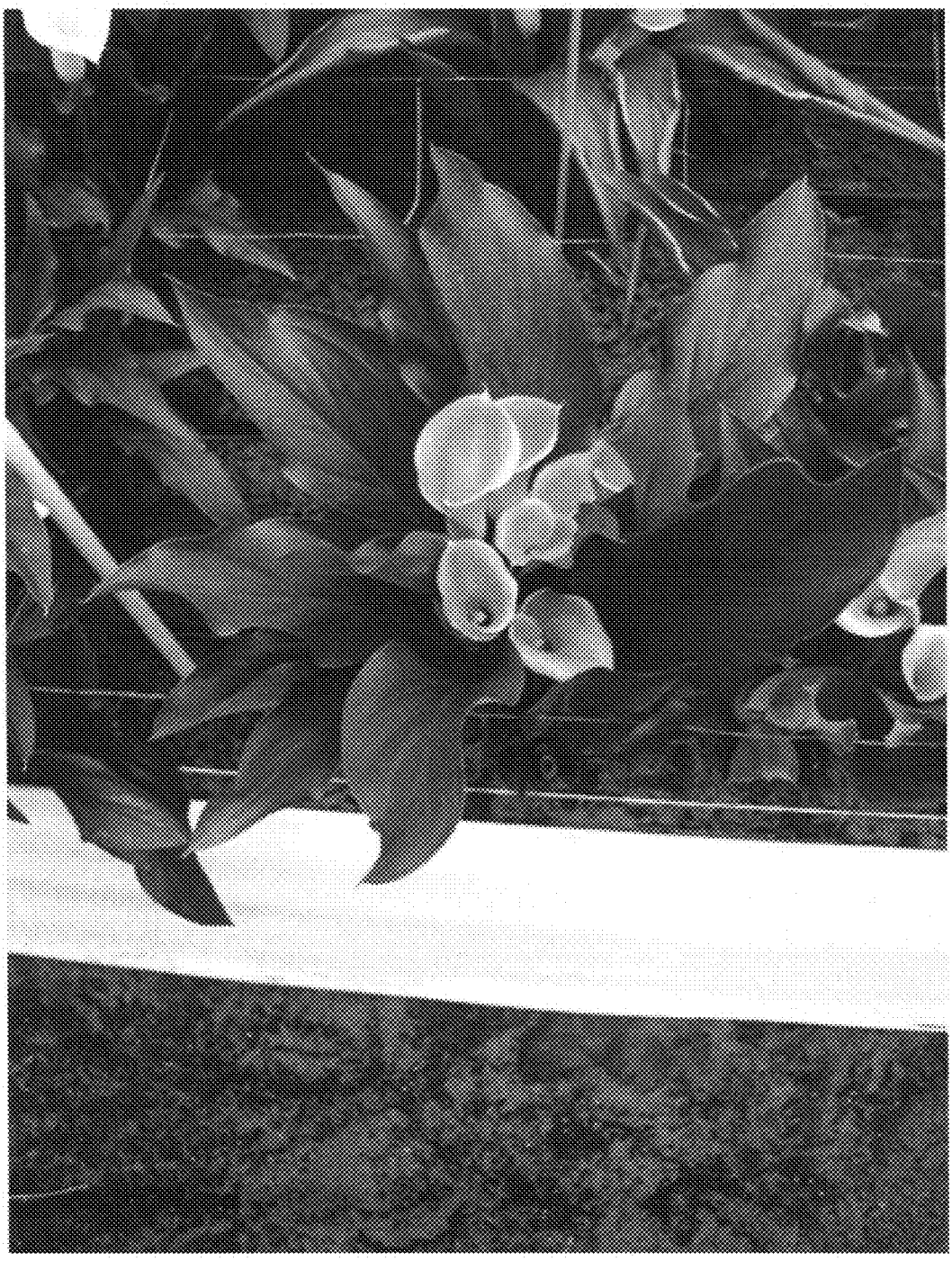
FIG. 3 is an overhead view of a single plant of the new variety.

Size:

*Height of the leaf canopy above the soil.*—7-45 cm.

*Height of top of inflorescence above the soil.*—20-40 cm.

*Diameter.*—20-45 cm.

Form: Erect.

Number of inflorescences per tuber:

*Size* 14-16 *cm in diameter.*—5-8 inflorescences.

*Size* 16-18 *cm in diameter.*—6-15 inflorescences.

*Size* 18-20 *cm in diameter.*—7-20 inflorescences.

Branches:

*Character.*—Many (from 3-10); like the variety 'Odessa' (U.S. Plant Pat. No. 18,833).

*Color.*—Between Yellow-Green Group RHS 146A and Greyed-Purple Group RHS 187A.

Leaves:

*Size.*—Width: 2.5-13 cm. Length: 10-25 cm.

*Number per plant.*—25-35.

*Shape.*—Lanceolate.

*Color.*—Upper surface: Green Group RHS 137A to 137B. Lower surface: Green Group RHS 137C to 137D.

*Apex.*—Acuminate.

*Base.*—Rounded.

*Margin.*—Undulate; having a color of Green Group RHS 137A to 137B.

*Veins.*—Configuration: Pinnate. Color: Green Group RHS 143A to 143B.

*Surface quality.*—Leathery.

*Petiole.*—Length: 6-25 cm. Diameter: 7 mm. Color: The base is White Group RHS 155A, and the upper part is Green Group RHS 143A and 143B.

Roots:

*Color.*—White.

*Branching.*—Similar to other *Zantedeschia* varieties.

The Inflorescence and Seeds

Spathe:

*Size.*—Length (measured from base opening to tip): 4-8 cm. Width: 4-6 cm. Height: 5-9 cm.

*Color.*—Upper surface: Varies between Red-Purple Group RHS 58A and 58B. Lower surface: Varies between Yellow-Green Group RHS 145C and 145D.

*Vein color.*—Between Red-Purple Group RHS 58A and 58B.

*Shape.*—Cupped.

*Apex.*—Apiculate.

*Base.*—Rounded.

*Texture.*—Smooth (upper and lower surfaces).

Spadix:

*Size.*—Length: 30-50 mm. Diameter: 4-9 mm.

*Color.*—Between Yellow Group RHS 11A and 11B.

*Position relative to spathe.*—Upright.

Peduncle:

*Size.*—Length: 15-35 cm. Diameter: 4-15 mm.

*Color.*—The upper part is between Yellow-Green Group RHS 144A and 144B, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow Group RHS 11A and 11B.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 13C and 13D.

*Ovaries.*—Texture: Smooth. Length: Between 1 to 10 mm. Width: Between 1 to 10 mm. Color: Top color is between Orange-White Group RHS 159A and 159B, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-50.

Fruit:

*Amount.*—Multiple berries produced.

*Shape.*—Irregular.

*Color.*—Varies between Yellow-Green Group RHS N145B and 145C with very few Red-Purple Group RHS 59D spots surrounding the stigma.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Forever' as herein described and illustrated.

* * * * *